United States Patent [19]

Skatulla et al.

[11] Patent Number: 5,180,474
[45] Date of Patent: Jan. 19, 1993

[54] METHOD OF SEPARATION OF AROMATES BY EXTRACTIVE DISTILLATION

[75] Inventors: Luzian Skatulla, Mühlheim an der Ruhr; Hans-Jürgen Vollmer, Essen; Hans-Christoph Schneider, Hattingen, all of Fed. Rep. of Germany

[73] Assignee: Krupp Koppers GmbH, Essen, Fed. Rep. of Germany

[21] Appl. No.: 825,946

[22] Filed: Jan. 27, 1992

[30] Foreign Application Priority Data

Mar. 23, 1991 [DE] Fed. Rep. of Germany ....... 4109632

[51] Int. Cl.$^5$ ............................. B01D 3/40; C07C 7/08
[52] U.S. Cl. ....................................... 203/84; 203/58; 203/99; 203/DIG. 9; 203/DIG. 19; 208/313; 208/325; 208/355; 208/365; 585/808; 585/865; 585/902
[58] Field of Search ..................... 203/58, 25, 84, 99, 203/DIG. 9, DIG. 19; 208/313, 325, 355, 365, 364; 585/808, 865, 902

[56] References Cited

U.S. PATENT DOCUMENTS

| | | | |
|---|---|---|---|
| Re. 22,379 | 9/1943 | Dunn et al. | 203/58 |
| 2,325,379 | 7/1943 | Durrum | 203/58 |
| 2,357,028 | 8/1944 | Shiras et al. | 203/84 |
| 2,379,110 | 6/1945 | Souders, Jr. | 203/84 |
| 2,842,484 | 7/1958 | Fleck | 203/58 |
| 3,399,120 | 8/1968 | Lovett | 203/84 |
| 3,434,936 | 3/1969 | Luther et al. | 203/58 |
| 3,554,873 | 1/1971 | Luther et al. | 203/58 |
| 3,723,256 | 3/1973 | Thompson | 203/84 |
| 3,775,259 | 11/1973 | Sarno | 203/84 |
| 3,798,132 | 3/1974 | Sarno | 203/99 |
| 3,868,310 | 2/1975 | Van Kleef et al. | 203/58 |
| 4,081,355 | 3/1978 | Preusser et al. | 208/313 |
| 4,168,209 | 9/1979 | Mikitenko et al. | 203/84 |
| 4,191,615 | 3/1980 | Schulze et al. | 203/58 |
| 4,278,505 | 7/1981 | Danulat et al. | 203/84 |
| 4,299,667 | 11/1981 | Klein et al. | 203/42 |
| 4,498,980 | 2/1985 | Forte | 208/321 |
| 4,925,535 | 5/1990 | Preusser et al. | 203/25 |
| 5,031,754 | 7/1991 | Emmrich et al. | 203/84 |

FOREIGN PATENT DOCUMENTS

| | | | |
|---|---|---|---|
| 1264740 | 2/1972 | United Kingdom | 203/58 |
| 1291029 | 9/1972 | United Kingdom | 203/58 |

*Primary Examiner*—Virginia Manoharan
*Attorney, Agent, or Firm*—Michael J. Striker

[57] ABSTRACT

A method of separation of aromates from hydrocarbon mixtures by extractive distillation with a selective solvent, includes introducing a hydrocarbon mixture into the extractive distillation column, distillating out non-aromate components of the introduced hydrocarbon mixture from a head of the extractive distillation column, withdrawing aromates together with a used solvent from a sump of the extractive distillation column and supplying to a driving-out column, separating the aromates from the solvent in the driving-out column, withdrawing the aromates as a head product and the solvent as a sump product from the driving-out column, reintroducing the withdrawn solvent into the extractive distillation column, the withdrawing of the solvent from the driving-out column including withdrawing only part of the solvent with a high temperature required for the complete aromate driving-out from the sump of the driving-out column, while a rest of the solvent with a certain aromate content and a lower temperature is withdrawn as a side stream from the driving-out column, reintroducing the side stream into the extractive distillation column at a location which is 6th-10th plate above an inlet for the solvent stream coming from the sump of the driving-out column.

4 Claims, 1 Drawing Sheet

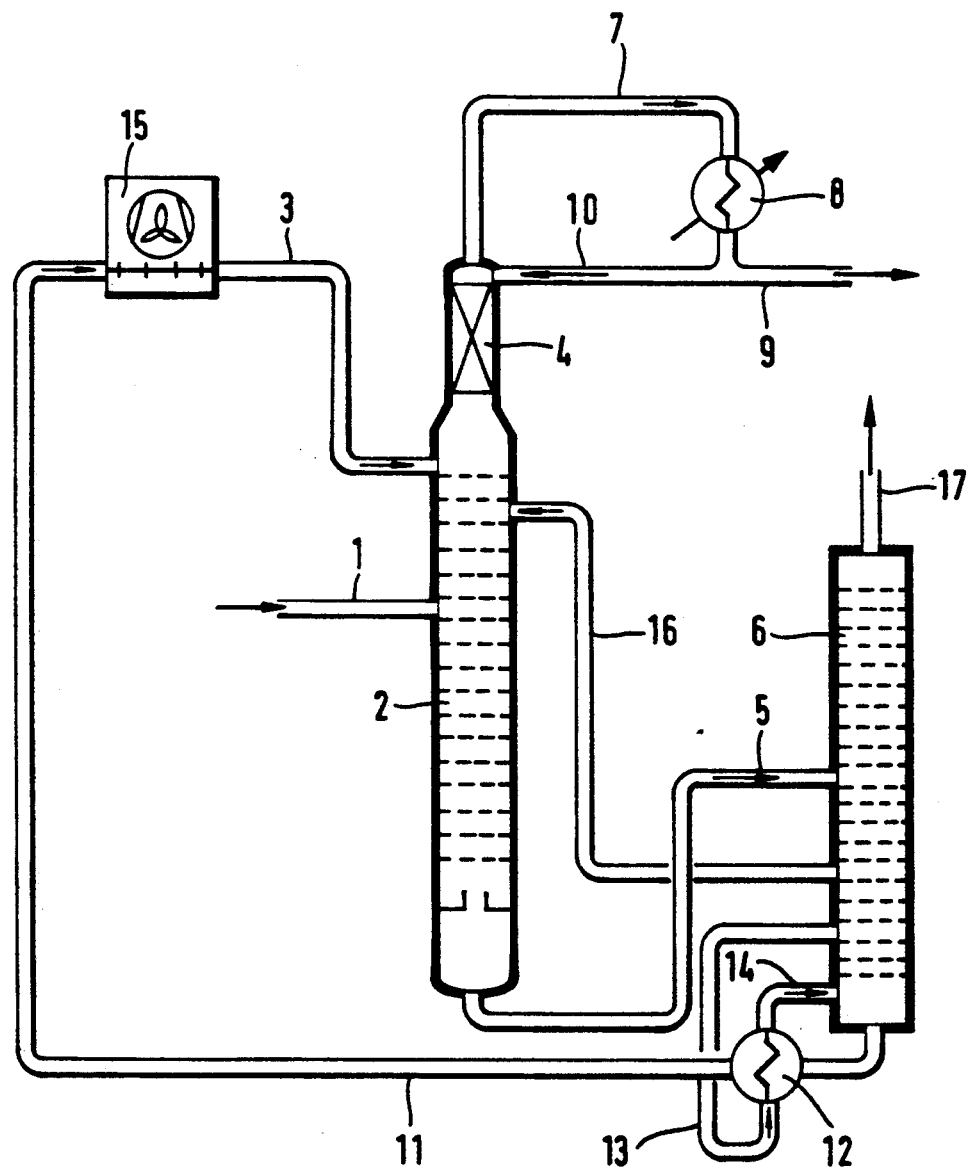

METHOD OF SEPARATION OF AROMATES BY EXTRACTIVE DISTILLATION

BACKGROUND OF THE INVENTION

The present invention relates to a method of separation of aromates from hydrocarbon mixtures of any aromate content by extractive distillation with a selective solvent.

More particularly, it relates to such a method in accordance with which the non-aromatic components of the hydrocarbon mixture which serves as an initial product are distillated off while the aromates together with the used solvents are withdrawn from the sump of the extractive distillation column and separated in a subsequent driving-out column in a distillative manner from the solvent. The aromates are withdrawn as a head product and the solvents as a sump product from the driving-out column, while the solvent is again reintroduced into the extractive distillation column.

During the utilization of the above mentioned method the maintenance of two conditions is necessary in practice. On the one hand, the non aromate content in the recovered aromates must not exceed a predetermined maximum value, and on the other hand the aromate losses must be as low as possible and the yield as high as possible. The fulfilling of this condition is however connected with certain energy consumption, since such extractive distillation processes are usually performed with the use of medium and high pressure vapor as an energy carrier. The medium pressure vapor serves first of all for heating the extractive distillation column, while the substantially more expensive high pressure vapor is required in the driving-out column for driving-out of the aromates from the solvent.

Due to the above described conditions, during the performance of a method of the above mentioned general type an economy of the energy cost must be taken in consideration when for recovering the energy consumption of the whole process, a part of the required high pressure vapor can be replaced by the less expensive medium pressure vapor.

SUMMARY OF THE INVENTION

Accordingly, it is an object of the present invention to provide a method of separation of aromates by extractive distillation, which achieves the above mentioned objects.

In accordance with the above mentioned method only a part of the solvent with the high temperature required for the complete aromate driving-out is withdrawn from the sump of the driving-out column, while the rest of the solvent with a certain aromate content and a lower temperature is withdrawn as a side stream from the driving-out column, while the side stream is again introduced at a certain location into the extractive distillation column which operates with a return flow, at six to ten plates underneath the inlet point for the solvent stream coming from the sump of the driving-out column.

In other words, during the inventive method two solvent circulating circuits are formed with different temperature and different aromate content. The invention proceeds from the recognition that during withdrawal of the total solvent with high temperature from the sump of the driving-out column, in practice only a part of the heat content of the withdrawn solvent can be used by the heat exchange process inside the whole method. Apart from the heat contents must always however, prior to the reintroduction of the solvent into the extractive distillation column, must be withdrawn by cooling unused to the atmosphere. When as in the present invention, only part of the solvent with higher temperature is withdrawn from the sump of the driving-out column, naturally the part of the residual heat which must be withdrawn unused to the atmosphere is naturally reduced. Simultaneously, the high pressure vapor consumption required for the heating of the driving-out column is reduced.

During the inventive method the temperature and the aromate content of the solvent withdrawn as a side stream from the driving-out column naturally depends on the length of the withdrawing location. The temperature is lower and the aromate content is higher with the increase in the height of the withdrawal point in the driving out column. The temperature in turn is also dependent on the boiling temperature of the aromate to be recovered as well as on the boiling temperature of the used solvent. For example during the recovery of benzol by the extractive distillation with N-formylmorpholins as solvent, the temperature of the solvent side stream with 149° C. and a benzol content is 2.78 percent by weight when the withdrawal of the side stream is performed 29 plates from above from the driving-out column. If the withdrawal from the driving-out column is performed 22 plates from above the temperature of the side stream is 134.4° C. and the benzol content is 3.67 percent by weight.

The separation of both solid solvent quantity circulating streams is performed preferably so that 55-60 percent by weight of the whole solvent average quantity is withdrawn from the sump and the rest as side stream from the driving-out column. While the solvent partial stream withdrawn from the sump of the driving-out column before its reintroduction in the extractive distillation column is cooled in a known manner for the solvent partial stream withdrawn as a side stream from the driving-out column, such a cooling is not provided. This however means that with this second partial stream an additional heat quantity is supplied to the extractive distillation column in its upper part. During the utilization of the inventive method in view of a good separation, it is advantageous to operate the extractive distillation column with an outside return flow in contrast to the conventional practice. For using the heat content of this second solvent partial stream, it is advantageous in accordance with another embodiment of the invention to provide that the extractive distillation column above the solvent outlet has an additional column portion for the separation of the solvent residue from the non-aromates.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

The single FIGURE of the drawings is a view showing a flow diagram of a method in accordance with the present invention with all those parts which are necessary for understanding of the invention, while auxiliary devices such as for example pump, circulating boiler, heat exchanger, measuring and control devices are not shown.

DESCRIPTION OF THE PREFERRED EMBODIMENTS

By the method of separation of aromates by extractive distillation an aromate containing hydrocarbon mixture which serves as the initial part is supplied through a conduit 1 into a central part of an extractive distillation column provided with a plurality of plates. The required selective solvent is supplied through a conduit 3 to the head of the extractive distillation column 2. Above the solvent delivery the extractive distillation column 3 has in this case an additional column part 4 which serves for separation of the solvent residual from the non-aromates. In the extractive distillation column 2 the separation of the initial product is performed under the action of the solvent in a known manner. In other words the introduced solvent flows over the plates of the column downwardly, and picks up the vaporous aromates. The liquid sump product which is composed of the solvent and the dissolved aromates in it is withdrawn through a conduit 5 from the extractive distillation column 2 and supplied through a driving-out column 6. In the driving-out column it is broken many times as a sump product identified as an extract into its components.

The non-aromate hydrocarbons of the initial hydrocarbon mixture which form the raffinate phase raise as a vapor in the extractive distillation column 2 upwardly. In order to withdraw the solvent residue from this non-aromate hydrocarbons, the extracted distillation column 2 is provided above the solvent delivery, for example above the opening of the conduit 3 of the column, with an additional column part 4. This column part 4 can be provided with plates or other inserts formed together with the extraction distillation column 2 a structural unit. In the shown embodiment the column part 4 has a substantially smaller diameter than the remaining extractive distillation column 2. In the practice, however, both parts can have the same diameter. The nonaromatic hydrocarbons released from the solid residues escape as a vapor through the shaft from the column part 4 and supplied through a conduit 7 into a cooler 8. In the cooler the hydrocarbons are condensed. The main quantity of the liquid non-aromates is subsequently withdrawn through the conduit 9 from the process and supplied to a further use, while a partial stream is again reintroduced through a conduit to a return flow to the head in the column part 4. The return flow quantity is adjusted so that the recovered non-aromates have the desired purity.

In accordance with the present invention, from the sump of the driving-out column 6 provided with the plates only a partial stream of the solvent with the high temperature required for the complete aromate driving-out is withdrawn through a conduit 11. As specified hereinabove, a part of the heat content of the partial stream can be used by the heat exchange within the whole process. As an example, in the shown diagram a sump circulating boiler 12 is provided in conduit 11, and it serves for heating of the sump product from the driving-out column 6. Through a conduit 13 the supply of the sump product to the sump circulating boiler 12 is performed, and through a conduit 14 the withdrawal is performed. Also other heat exchange processes for the utilization of the heat content of the hot solvent can be naturally used in the whole process. Since this is however not the object of the present invention, it is not described in detail. What is important for the invention is that in this manner only a part of the heat content can be used. The still available residual heat must be therefore withdrawn unused, and the solvent is introduced through the conduit 11 into the circulating boiler 15 in which it is cooled to the temperature with which it can be again reintroduced through the conduit 3 into the extractive distillation column 2. Since in accordance with the present invention only between 55-60 weight percent of the whole solvent quantity is withdrawn through the conduit 11 from the driving out column 6, naturally the heat quantity which must be guided unused through the air cooler 15 must be correspondingly reduced.

The remaining solvent is withdrawn through a conduit 16 as a side stream from the driving-out column 6 and introduced into the extractive distillation column 2 6th-10th plates underneath the inlet point of the conduit 3. In the driving-out column with total 75 plates, the withdrawal point for this side stream can be for example between 16th and 24th plate from above. As mentioned hereinabove, the temperature of the side stream is lower and the aromates content is higher with the increase in the height of the withdrawal plate in the driving-out column 6. Since the solvent partial stream withdrawn through the conduit 16 before its reintroduction into the extractive distillation column 2 has no cooling, in accordance with a preferable embodiment of the inventive method the extractive distillation column 2 is provided with the above described additional column part 4. In this part the heat content of the solvent partial stream supplied through the conduit 16 for the removal of the solvent residual from the raffinate is utilized. The aromates released from the solvent are withdrawn through a conduit 17 from the driving-out column 6.

The efficiency of the inventive method is connected with the following experimental conditions. The separation of benzol by the extractive distillation with N-formylmorpholin as selective solvent is performed. As the initial product a raw benzol fraction is utilized. In a first part of these experiments the extractive distillation is performed under the conventional conditions, while the extractive distillation column is heated with the medium pressure vapor and the driving-out column with high pressure vapor. In other words, the solvent released from the aromate is as a whole withdrawn from the sump of the driving-out column and after corresponding cooling is resupplied to the extractive distillation column which operates without the return flow. The non-aromate content recovered benzol is 170 ppm and the benzol yield amounts to 99.1%.

In the second part of the experiments the unchanged process conditions were used in accordance with the present invention with two solvent circulation circuits. Here approximately only 57 percent by weight of solvent is withdrawn through the conduit 11 from the driving-out column 6. For the remaining solvent withdrawal is performed as a side stream through the conduit 16. The withdrawal of the side stream is performed 29 plates from above for the driving-out column 6 having a total of 31 plates. The temperature of the side stream is 149° C. and the withdrawal content is 2.78 percent by weight. The side stream is introduced 7 bottoms underneath the inlet of the conduit 3 in the extractive distillation column. With the return flow condition in the extractive distillation column equal to 2.3 in this case the comparative value of 170 ppm non-aromates in the recovered benzol is achieved. With a return flow condition of 2.0, the comparative value falls under.

In a further experiment, the solvent side stream is withdrawn 22 plates from above from the driving out column 6 and introduced 7th plates under the inlet of the conduit 3 in the extractive distillation column 2. The temperature of the side stream in this case is 134.3° C. and the benzol content is 3.67 percent by weight. The comparison value of 170 ppm non-aromates in the recovered benzol is achieved here at a return flow condition in the extractive distillation column of 1.8.

In the above presented experiments, it is shown that the inventive extractive distillation with two solvent circulating streams is performed, and at least leads to the same good conditions as in the conventional operation. The presented calculations show that the energy consumption for the whole process with the use of the inventive operation is performed however a displacement of heat supply from the driving column 6 to the extractive distillation column 2 which leads to a reduction of the high pressure vapor consumption with simultaneous increase in the medium pressure vapor consumption. During the withdrawal of the solvent side stream from the 29th plate of the driving-out column 6, the high pressure vapor consumption is only approximately 75% of the value for the first part of the experiments of the above performed comparative experiments. During the withdrawal of the solvent side stream from the 22nd plate of the driving-out column, this value is lowered to approximately 55 percent of the value for the comparative experiment. Due to the cost relation between the high pressure and medium pressure vapor there is a considerable saving of the operational cost.

The above presented results find a clarification first of all in that in the inventive operation only a part of the solvent is heated to the high temperature required for the complete aromate withdrawal. On the other hand, it should be taken into consideration that in this case in the sump of the driving-out column significantly less solvent must be evaporated as required for an internal return flow into the lower part of the driving-out column. The lower the aromate content in the solvent mass be, the more solvent must evaporate. This naturally drives the high pressure vapor consumption.

It will be understood that each of the elements described above, or two or more together, may also find a useful application in other types of methods differing from the types described above.

While the invention has been illustrated and described as embodied in a method for separation of aromates from hydrocarbon mixtures, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A method of separation of aromates from hydrocarbon mixture by extractive distillation with a selective solvent, comprising introducing a hydrocarbon mixture into the extractive distillation column, distillating out non-aromate components of the introduced hydrocarbon mixture from a head of the extractive distillation column; withdrawing aromates together with a used solvent from a sump of the extractive distillation column and supplying to a driving out column; separating the aromates from the solvent in the driving-out column; withdrawing the aromates as a head product and the solvent as a sump product from the driving-out column; reintroducing the withdrawn solvent into the extractive distillation column, said withdrawing of the solvent from the driving-out column including withdrawing only a part of the solvent as a solvent partial stream with a higher temperature and a lower aromate content from the sump of the driving out column, while a remaining portion of the solvent with a higher aromate content and a lower temperature is withdrawn as a side stream from the driving-out column; reintroducing the side stream into the extractive distillation column at a location which is 6–10 plate below an inlet from the solvent stream coming from the sump of the driving-out column, and separating residual solvent from the recovered non-aromates in an additional column located above the extractive distillation column.

2. A method as defined in claim 1, wherein 55–60 percent by weight of the solvent quantity is withdrawn from the sump and the remaining portion of the solvent is withdrawn as a side stream from the driving-out column.

3. A method as defined in claim 1; and further comprising the step of cooling the solvent partial stream withdrawn from the sump of the driving-out column before its introduction into the extractive distillation column while the solvent withdrawn as a side stream from the driving-out column is not subjected to cooling prior to its reintroduction into the extractive distillation column.

4. A method as defined in claim 1, wherein the extractive distillation column operates with a return flow ratio of 1.5–2.5.

* * * * *